(12) United States Patent
Fateh

(10) Patent No.: US 10,251,544 B2
(45) Date of Patent: Apr. 9, 2019

(54) HEAD-MOUNTED DISPLAY FOR PERFORMING OPHTHALMIC EXAMINATIONS

(71) Applicant: Kali Care, Inc., Mountain View, CA (US)

(72) Inventor: Sina Fateh, Mountain View, CA (US)

(73) Assignee: KALI CARE, INC., Mountain View, CA (US)

( * ) Notice: Subject to any disclaimer, the term of this patent is extended or adjusted under 35 U.S.C. 154(b) by 116 days.

(21) Appl. No.: 14/706,854

(22) Filed: May 7, 2015

(65) Prior Publication Data
US 2016/0324416 A1  Nov. 10, 2016

(51) Int. Cl.
*A61B 3/032* (2006.01)
*A61B 3/00* (2006.01)

(52) U.S. Cl.
CPC ............. *A61B 3/032* (2013.01); *A61B 3/005* (2013.01); *A61B 3/0025* (2013.01); *A61B 3/0033* (2013.01)

(58) Field of Classification Search
CPC . A61B 3/032; A61B 3/0025; A61B 3/02–3/09
USPC .......................................... 351/223; 345/7–8
See application file for complete search history.

(56) References Cited

U.S. PATENT DOCUMENTS

| 4,971,434 A | * | 11/1990 | Ball | A61B 3/024 |
| | | | | 351/224 |
| 6,003,991 A | * | 12/1999 | Viirre | A61B 3/145 |
| | | | | 348/E13.014 |
| 6,108,634 A | | 8/2000 | Podnar et al. | |
| 2011/0267577 A1 | * | 11/2011 | Verma | A61B 3/0033 |
| | | | | 351/201 |
| 2013/0335707 A1 | * | 12/2013 | Meuse | A61B 3/032 |
| | | | | 351/239 |
| 2017/0065168 A1 | * | 3/2017 | Bex | A61B 3/08 |
| 2017/0156586 A1 | | 6/2017 | Fateh | |

FOREIGN PATENT DOCUMENTS

JP  2007267802 A  10/2007

OTHER PUBLICATIONS

International Search Report and Written Opinion PCT/US2016/030590 dated Sep. 1, 2016, pp. 1-7.

* cited by examiner

*Primary Examiner* — Kristina M Deherrera
(74) *Attorney, Agent, or Firm* — Perkins Coie LLP

(57) ABSTRACT

Various embodiments relate to systems and methods for performing eye examinations using an HMD that is able to present an image to each eye individually and then to both eyes simultaneously. Because the HMD, rather than a patient, controls conditions (e.g., glare, brightness) during the examination, test results are more likely to be accurate and reliable. In some embodiments, the HMD employs voice recognition to replicate the conversational exchange that would typically occur between the patient and the ophthalmologist or optometrist. The HMD may also be configured to change the visual environment experienced by the patient during testing. Further yet, the HMD, or another distinct computing system, may be configured to identify abnormal test results in real-time and, in some embodiments, the examination is modified accordingly. For example, tests scheduled to be performed during the examination can be modified or removed and new tests can be added.

18 Claims, 11 Drawing Sheets

HEAD-MOUNTED DISPLAY FOR PERFORMING OPHTHALMIC EXAMINATIONS

FIELD OF THE INVENTION

Various embodiments concern systems and methods for performing ophthalmic examinations. More specifically, various embodiments relate to head-mounted displays (HMDs) that allow ophthalmic examinations to be performed in the absence of traditional testing equipment.

BACKGROUND

Ophthalmic examinations, also referred to as eye examinations, include a series of tests designed to evaluate the vision and eye health of a patient. Such tests, which are conventionally done by ophthalmologists or optometrists, can measure visual acuity, visual field, pupil constriction, color sensitivity, etc. Traditionally, specialized instruments were necessary and, consequently, the examination generally took place in a specialized office configured for ophthalmology or optometry.

The limited availability of ophthalmologists and optometrists meant that appointments were generally required before testing could be done. But scheduling long-range appointments can be problematic for a number of reasons. For example, patients rarely know their schedule days or weeks in advance. As another example, some eye diseases and vision problems develop rapidly and without warning, but require immediate attention. Further yet, ophthalmologist and optometrist offices may be inconveniently located, particularly for rural residents.

A variety of possible solutions have been proposed, but none are able to provide widely-available ophthalmic examinations that continue to be as effective, or nearly as effective, as traditional examinations. For example, various systems propose using the display of a cellular phone, tablet, etc., to perform examinations. But the validity of results of such examinations is often questionable. For example, a patient may not adequately block one eye when checking visual acuity of the opposite eye.

BRIEF DESCRIPTION OF THE DRAWINGS

These and other objects, features, and characteristics will become more apparent to those skilled in the art from a study of the following Detailed Description in conjunction with the appended claims and drawings, all of which form a part of this specification. While the accompanying drawings include illustrations of various embodiments, the drawings are not intended to limit the claimed subject matter.

Figure 1:
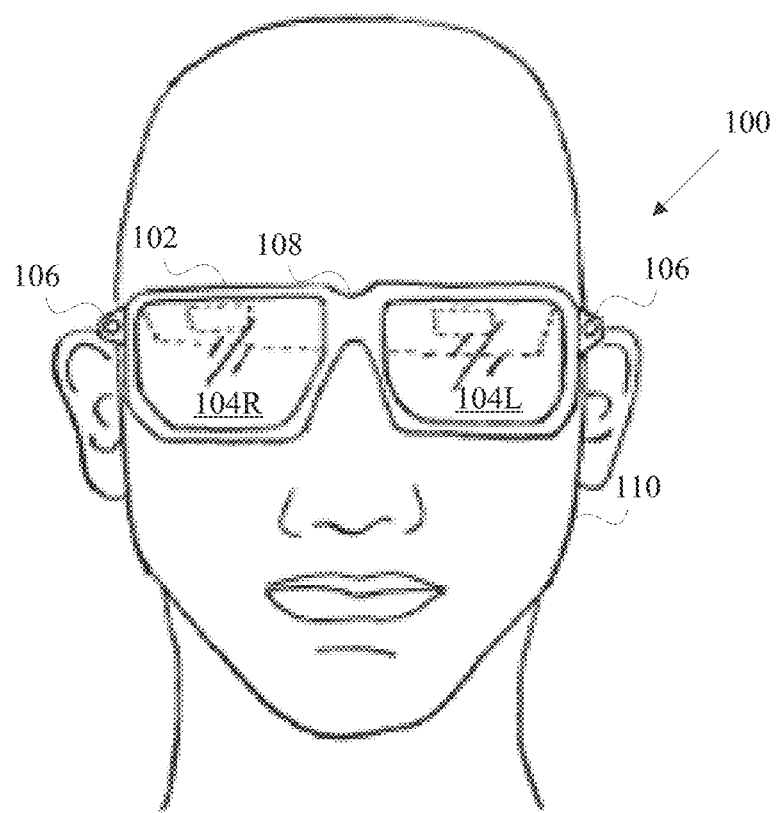
FIG. 1 is a front view representation of an HMD worn by a patient according to various embodiments.

The figures depict various embodiments described throughout the Detailed Description for purposes of illustration only. While specific embodiments have been shown by way of example in the drawings and are described in detail below, the invention is amenable to various modifications and alternative forms. The intention, however, is not to limit the invention to the particular embodiments described. Accordingly, the claimed subject matter is intended to cover all modifications, equivalents, and alternatives falling within the scope of the invention as defined by the appended claims.

DETAILED DESCRIPTION

Various embodiments are described herein that relate to systems and methods for performing eye examinations. More specifically, various embodiments relate to systems and methods for performing eye examinations using an HMD that is able to present an image to each eye individually and then to both eyes simultaneously. Because the HMD, rather than a patient, is able to control conditions (e.g., glare, brightness) during the examination, test results are more likely to be accurate and reliable. In some embodiments, the HMD employs voice recognition to replicate the conversational exchange that would typically occur between the patient and the ophthalmologist or optometrist. The HMD may also be configured to change the visual environment experienced by the patient during testing. Examinations that take place in more natural settings may cause the patient to feel less stressful. Further yet, the HMD, or another distinct computing system, may be configured to identify abnormal test results in real-time and, in some embodiments, the examination is modified accordingly. For example, tests scheduled to be performed during the examination can be modified or removed and new tests can be added.

Terminology

Brief definitions of terms, abbreviations, and phrases used throughout this application are given below.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. For example, two devices may be coupled directly, or via one or more intermediary channels or devices. As another example, devices may be coupled in such a way that information can be passed there between, while not sharing any physical connection with one another. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware (or any combination thereof) components. Modules are typically functional components that can generate useful data or other output using specified input(s). A module may or may not be self-contained. An application program (also called an "application") may include one or more modules, or a module can include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that same element can be described in more than one way.

Consequently, alternative language and synonyms may be used for any one or more of the terms discussed herein, and special significance is not to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

System Topology Overview

FIG. 1 is a front view representation of an HMD 100 worn by a patient 110 according to various embodiments. Light is emitted by the HMD 100 (e.g., by an image display system) and reflected by an optical display surface towards the patient's eye. The HMDs described herein are generally configured to display simulated (e.g., computer-generated) images of a virtual environment. That is, the HMD 100 can generate and present completely immersive "virtual reality" environments to a patient 110 during an eye examination. Convincing virtual reality typically requires a helmet, goggles, etc., that form an enclosed area around the patient's eyes and prevent contamination from ambient light, sound, etc. However, in some embodiments the HMD 100 may be configured to display simulated (e.g., computer-generated) images that are integrated into real world content perceived by the patient, also referred to as "augmented reality."

The projection and presentation systems employed by HMDs fall into three general categories: binocular, bi-ocular, and monocular. Binocular systems present a separate image to each of the user's eyes, while bi-ocular systems present a single image to both of the user's eyes, and monocular HMD systems present a single image to one of the user's eyes. Each of these systems could be used in various instances. For example, HMD 100 of FIG. 1 employs a binocular system and is able to present a distinct image to each of the patient's eyes.

The binocular HMD 100 includes various components and modules that allow eye examinations to be performed. Such components can include a frame 102, optical display surfaces 104L, 104R, an image display system, and one or more sensors 106. While the binocular HMD 100 of FIG. 1 resembles conventional glasses, the HMD could resemble goggles, a helmet, a visor, etc.

In some instances, a specialized HMD is used by the patient 110 that is designed for performing eye examinations. In other instances, various systems and methods described herein are implemented using an HMD already owned by the patient. More specifically, various methods introduced below could be performed using an HMD designed for another purpose (e.g., gaming, entertainment).

As described above, a binocular HMD 100 includes an optical display surface 104L for the patient's left eye and an optical display surface 104R for the patient's right eye (collectively referred to as "optical display surface 104"). Such a configuration allows content to be presented to each of the user's eyes individually, as well as both eyes collectively. The optical display surface 104 may completely surround one or both eyes of the patient. For example, the frame 102 and bridge 108 can be designed to ensure that light (e.g., an image) presented to one eye cannot be seen by the other eye. The HMD 100 allows digital images to be shown to one eye, while limiting what, if anything, can be seen by the other eye.

The HMD 100 can also include an electronics module that processes digital content (e.g., images, video), analyzes data collected by the one or more sensors 106, optimizes digital content to be presented to the patient, etc. As will be described more in-depth below, the electronics module allows at least some analysis (e.g., of test results) to be performed locally on the HMD 100. In some embodiments, the HMD 100 is communicatively connected to one or more other computing devices (e.g., cellular phones, tablets, computers, servers) that are also able to assist in performing some or all of these tasks. The electronics module and HMD 100 can be powered through a wired or wireless (e.g., battery) medium.

In some embodiments, one or more sensors 106 are coupled to the frame 102 and/or optical display surface 104 to monitor various aspects of the patient's local environment. For example, the sensor(s) 106 may include an audio sensor (e.g., microphone) and speaker that allow the patient to audibly communicate during the eye examination. The sensors 106 may also include a camera configured to capture the user's interactions with the local environment, a light sensor configured to track ambient illuminance levels, etc.

Figure 2A:
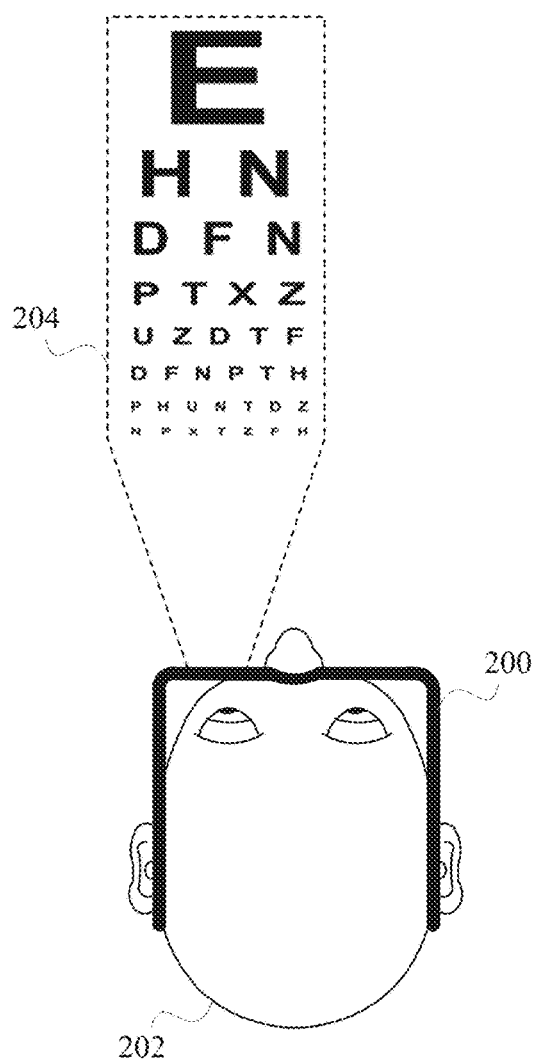
FIGS. 2A-C are diagrammatic illustrations of a patient's view using the left eye, right eye, and both eyes as may be experienced in some embodiments.
Figure 2B:
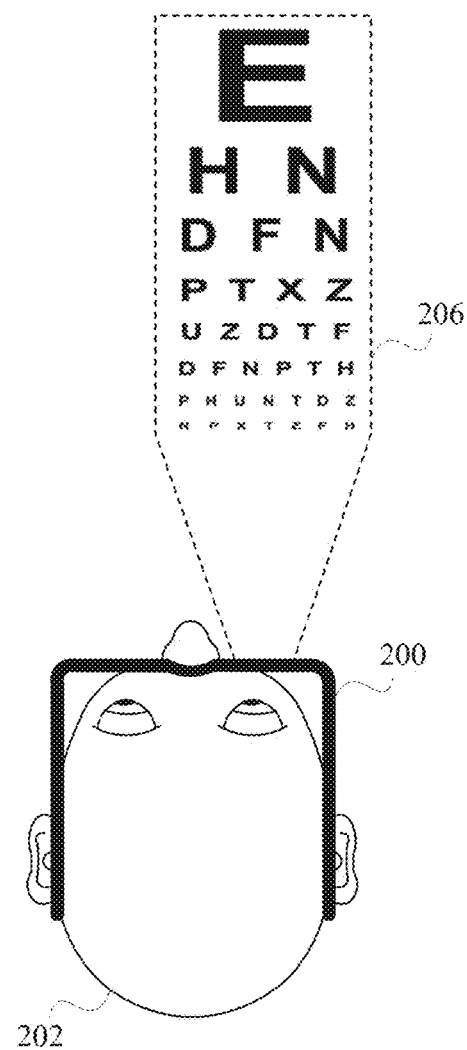
Figure 2C:
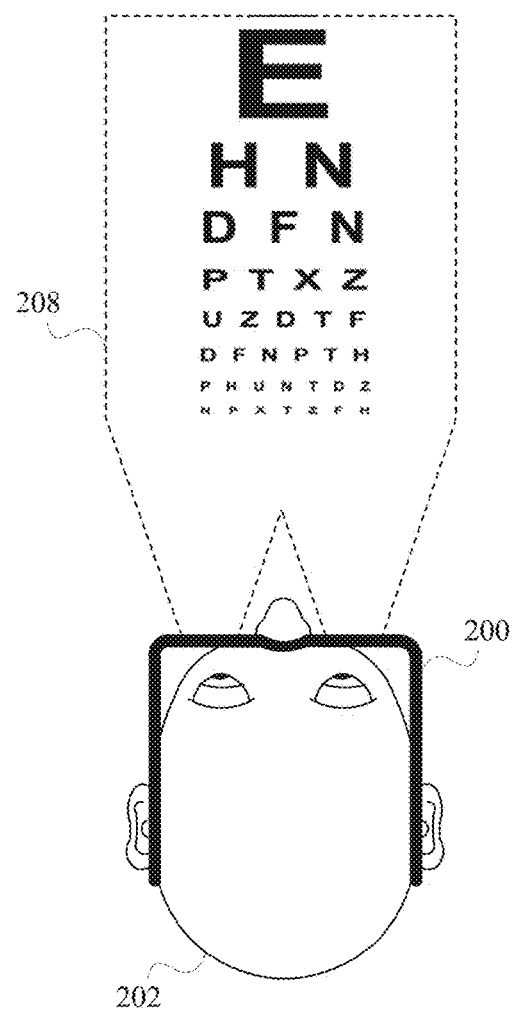

FIGS. 2A-C are diagrammatic illustrations of a patient's view using the left eye, right eye, and both eyes as may be experienced in some embodiments. Here, an HMD 200 is configured to project an image (e.g., Snellen chart) to each eye separately and then to both eyes together. By projecting to each eye separately, the HMD 200 is able to simulate an ophthalmologist or optometrist covering one eye while testing the vision of the other eye. Consequently, the HMD 200, rather than the patient 202, is able to control what can be seen by each eye while tests are being performed.

FIG. 2A figuratively depicts an image 204 that is shown only to the patient's left eye. Tests for visual acuity, visual field, etc., can be performed on the left eye, while the image 204 remains unseen by the right eye. FIG. 2B, meanwhile, figuratively depicts an image 206 that is shown only to the patient's right eye. The HMD 200 (e.g., using the electronics module) can control which image(s) are shown to which eye(s). Some tests, for example, may require the HMD 200 present an image 208 to both eyes simultaneously, as shown in FIG. 2C.

Alternatives to traditional eye examinations typically fail to adequately control or account for conditions that impact test results, such as glare, image brightness, humidity, etc. For example, applications (e.g., for cellular phones, tablets) are unable to account for glare on the screen or determine whether the patient has completely covered an eye during testing. However, the HMDs described herein allow conditions and contaminants to be closely monitored and/or kept consistent. HMD 200 of FIGS. 2A-C, for instance, can prevent glare while conducting the eye examination.

Figure 3:
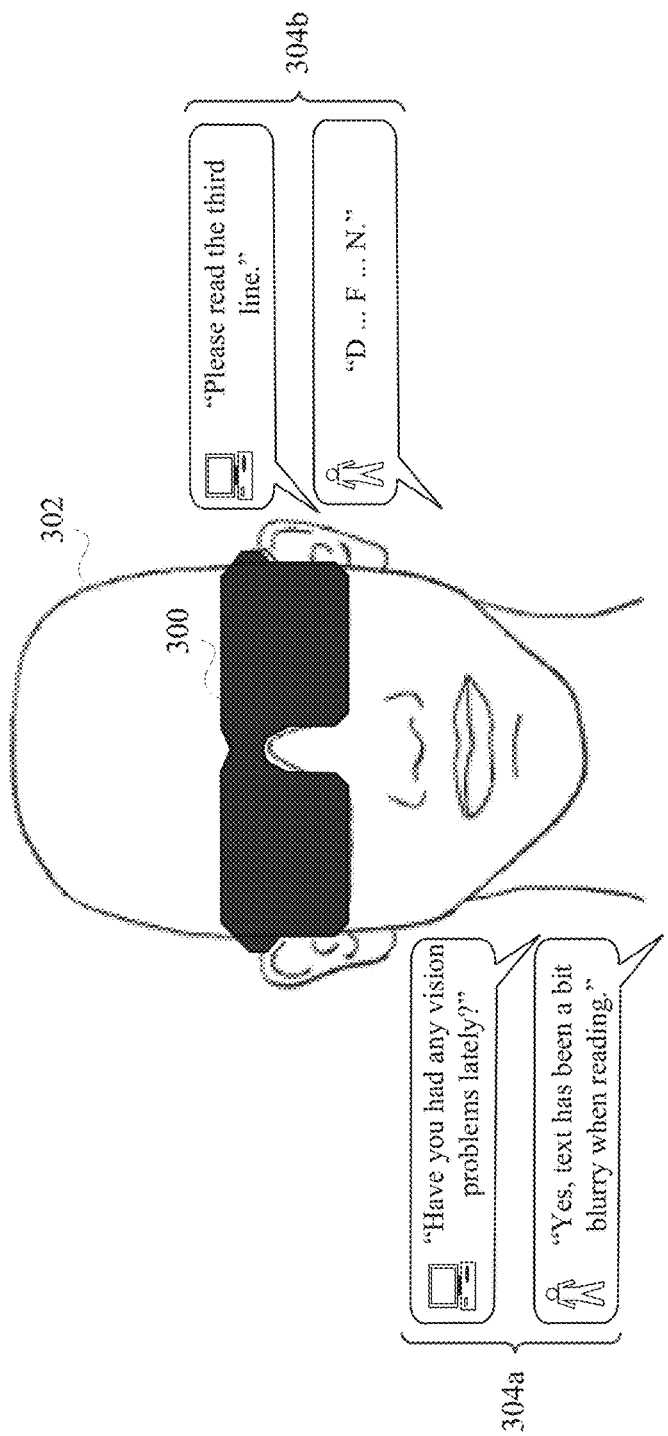
FIG. 3 depicts sample conversational exchanges as may occur when an HMD employs voice recognition techniques.

FIG. 3 depicts sample conversational exchanges as may occur when an HMD 300 employs voice recognition techniques. In some embodiments, the HMD 300 includes an audio sensor (e.g., microphone) and a speaker. The audio sensor is able to record audible conversational elements (e.g., responses, questions) given by the patient. Voice/speech recognition can be used to translate the audible conversational elements into text and determine whether keywords, key phrases, etc., were spoken by patient. Particular modules (e.g., speech recognition module, analysis module) may be used to perform some or all of these steps. Thus, the HMD 300 is able to replicate conversational exchanges between the patient and an ophthalmologist or optometrist. In some embodiments, natural language processing (NLP) and/or machine learning (ML) may be employed to improve the effectiveness of speech recognition, the selection of appropriate conversational elements, etc.

In some embodiments, the HMD 300 is completely or semi-autonomous (i.e., no human action is necessary) in determining what responses, inquiries, etc., are appropriate under the circumstances. In other embodiments, the HMD 300 allows an ophthalmologist or optometrist to provide feedback from a remote location (i.e., audible supervision can be provided while the examination is performed).

Various tests conducted during the examination may require the patient 302 provide feedback. For example, the HMD 300 begin a conversational exchange 304*a-b* by making a statement ("Please read the third line.") and waiting for a response. Once an audible response ("D . . . F . . . N.") is received, the HMD 300 can perform vocal recognition. Recognized elements, such as letters, words, and phrases, may be used to modify the examination. For example, wrong answers and certain keywords (e.g., "blurry," "fuzzy") may indicate additional testing is necessary. Keywords and phrases (e.g., "pressure within eye") may also reveal potential symptoms (e.g., of an eye disease) that can be tagged as needing additional testing. As will be described more in-depth below, elements recognized within the patient's responses can also be used to modify the examination itself.

Figure 4:
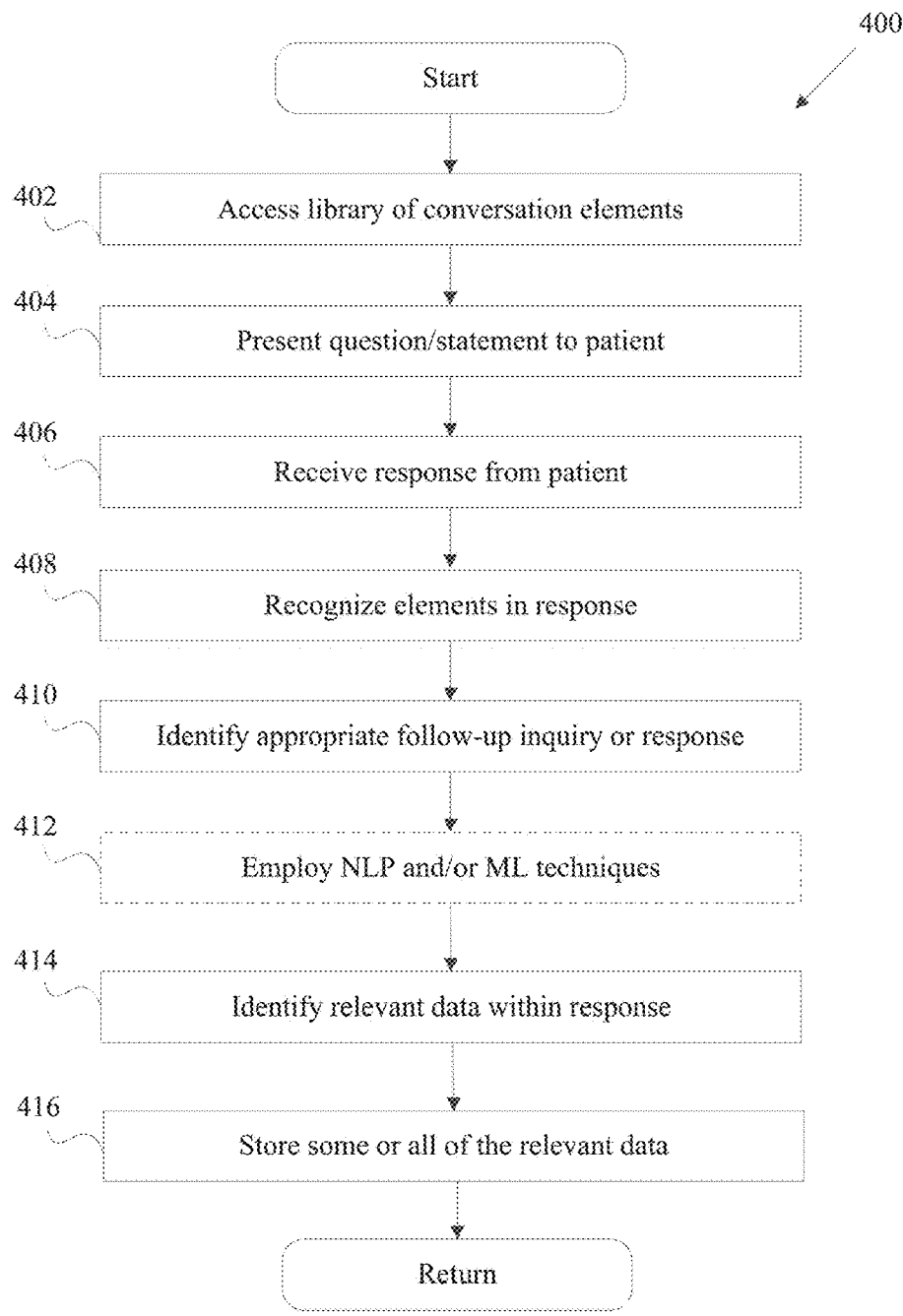
FIG. 4 is a flow diagram depicting a process for performing eye examinations as may occur in various embodiments.

FIG. 4 is a flow diagram depicting a process 400 for performing eye examinations as may occur in various embodiments. At block 402, an HMD can access a library of conversation elements, such as inquiries and responses. In some embodiments the library of conversation elements is stored locally (e.g., within a storage of the HMD), while in other embodiments the library of conversation elements is stored remotely (e.g., on a remote storage communicatively coupled to the HMD).

At block 404, the HMD presents question, statement, etc., to a patient that is intended to elicit a response. The question, statement, etc., may seek to elicit specific or general information from the patient that can be used during the eye examination. For example, the HMD may ask, "Have you experienced any eye or vision issues since your last examination?" As another example, the HMD may ask, "What is the smallest line of readable characters on the Snellen chart?" Wrong or unexpected answers may be flagged for additional follow-up. At block 406, the HMD receives a response from the patient. Generally, the response is audible, although other methods of communication (e.g., typing, gesture recognition) may also be used.

At block 408, the HMD can recognize elements within the response received from the patient. Various embodiments can employ text, gesture, and/or speech recognition depending on how the patient elects to respond. Recognized elements (e.g., words, phrases) can be used to identify an appropriate follow-up inquiry or response, as shown at block 410. For example, if the speech recognition indicates the patient recited a line from the Snellen chart incorrectly, the HMD may ask the patient to repeat the same line or recite a different line. In some embodiments, NLP and/or ML techniques are employed to improve recognition of keywords and phrases, as shown at block 412. The NLP and/or ML can be performed locally by the HMD, remotely by a distinct computing device (e.g., cellular phone, tablet, computer, server), or both.

At block 414, the HMD and/or the distinct computing device can identify relevant data within the response. The relevant data may be expected (e.g., recitation of numbers within Ishihara Color Vision Test) or unexpected (e.g., unprompted response describing a recent symptom). At block 416, some or all of the relevant data is stored by the HMD and/or the distinct computing device. The relevant data may be stored, for example, in a database entry corresponding to the patient. In some instances, all relevant data may be kept (e.g., an entire patient response that indicates increased risk of eye disease). In other instances, a subset or summary of the relevant data may be kept (e.g., a notification the patient passed Ishihara Color Vision Test).

Figure 5A:
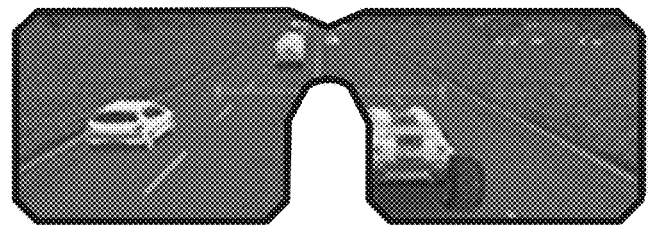
FIGS. 5A-C are pictorial illustrations of visual environments as may be presented by the HMD in some embodiments.
Figure 5B:
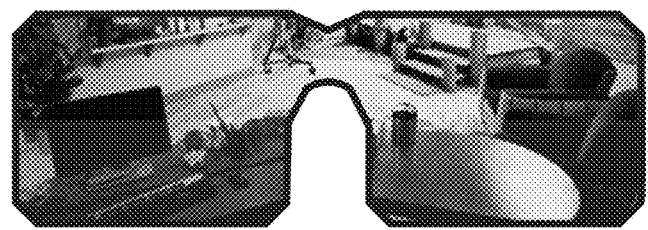
Figure 5C:
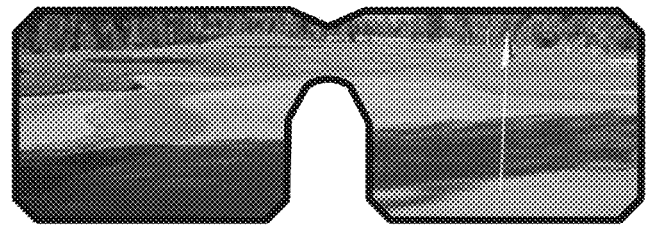

FIGS. 5A-C are pictorial illustrations of visual environments as may be presented by the HMD in some embodiments. Eye examinations are typically conducted within an ophthalmologist's or optometrist's office, an artificial environment designed specifically for testing. In some embodiments, an HMD can modify the visual environment in which the eye examination takes place. For example, FIGS. 5A-C depict a video game, an office setting, and a golf course, respectively. Other visual environments are also possible and may be supplied by the patient, other HMD users, etc. The visual environments can be stored in a library from which the patient or HMD can select.

The modifiable and customizable visual environments described herein may improve the effectiveness of visual field testing, which maps patient responses to visual stimuli to identify gaps in the field of vision. That is, the HMD can perform visual field testing in a more natural setting by modifying the visual environment.

Figure 6:
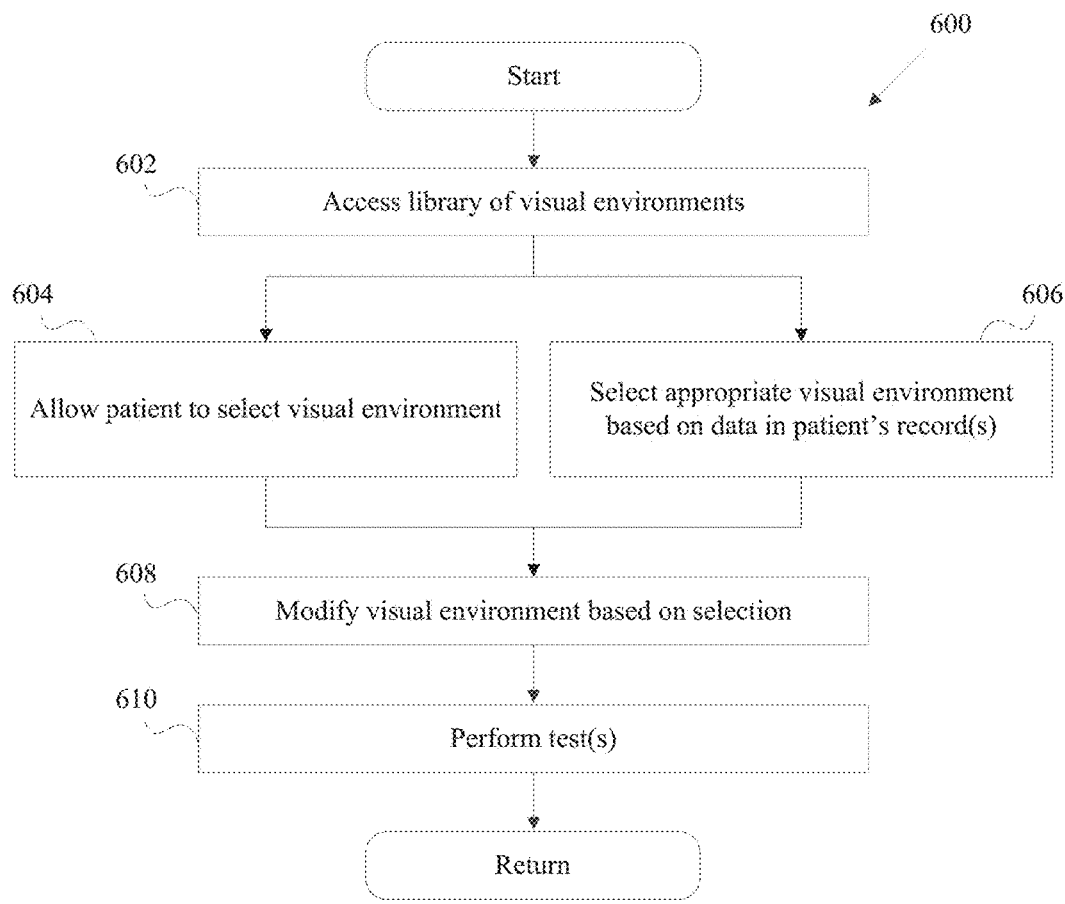
FIG. 6 is a flow diagram of a process for modifying the visual environment in which the eye examination takes place as may occur in some embodiments.

FIG. 6 is a flow diagram of a process 600 for modifying the visual environment in which the eye examination takes place as may occur in some embodiments. At block 602, the HMD can access a library of visual environments. The library may be stored locally within a storage or memory of the HMD system or remotely in a storage to which the HMD system is communicatively coupled. Users of other HMDs, including other patients, may be allowed to upload visual environments to the library that can be downloaded and used by others.

In some embodiments, the HMD allows the patient to select which visual environment will be used during the eye examination, as shown at block 604. In other embodiments, the HMD selects an appropriate visual environment from the library based on data within the patient's record(s), as shown at block 606. The data may come from records or entries within a database that stores information supplied by the patient, recorded during previous examinations, gleaned from patient responses, etc.

At block 608, the visual environment can be modified based on the selection made by the patient or HMD. At block 610, the HMD can perform one or more tests that are required by the examination. The visual environment may be presented during the entire examination or only during particular tests.

Figure 7:
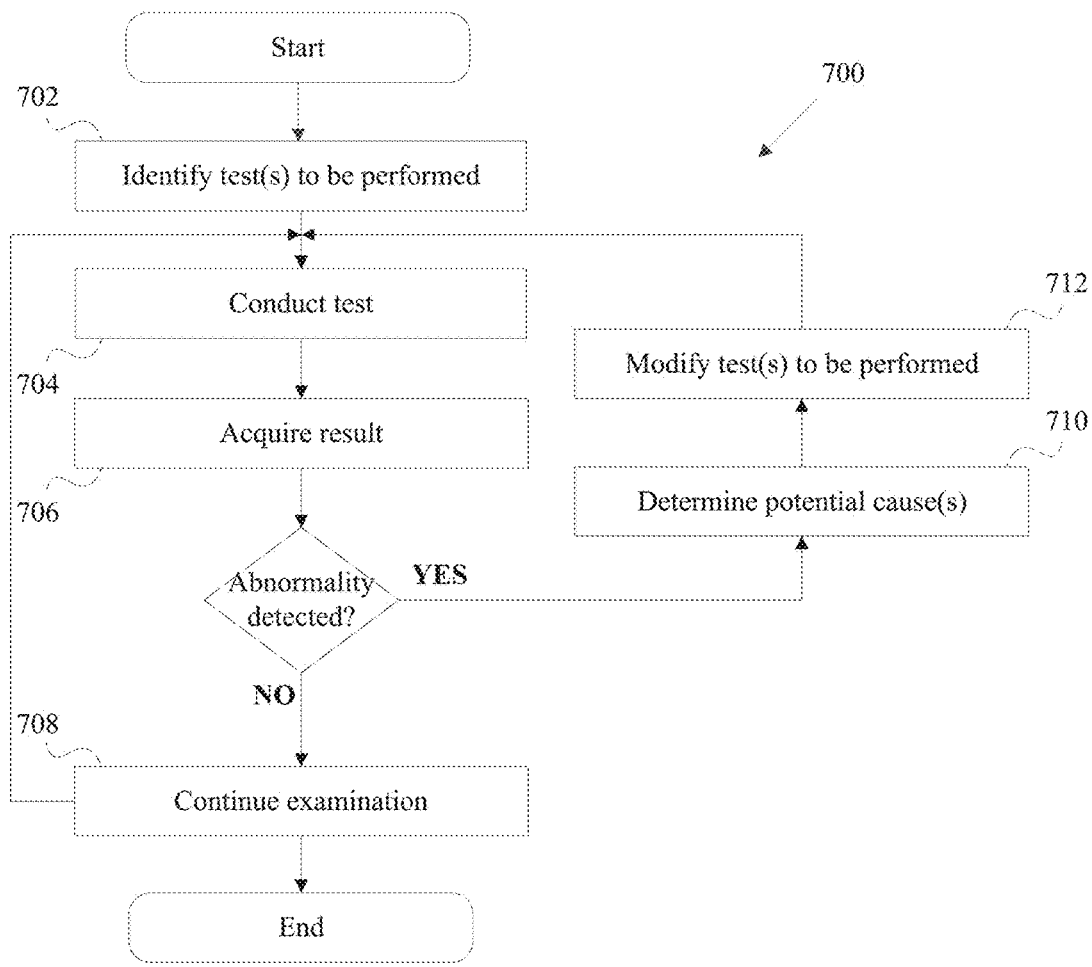
FIG. 7 is a flow diagram of a process for adapting an eye examination in real-time based on results gathered during the examination as may occur in some embodiments.

FIG. 7 is a flow diagram of a process 700 for adapting an eye examination in real-time based on results gathered during the examination as may occur in some embodiments. At block 702, the HMD identifies which one or more tests are to be performed during the examination. The one or more tests may be selected for a particular patient based on the results of previous examinations, patient response(s), recommendations from ophthalmologists and/or optometrists, etc. One skilled in the art will recognize the HMDs described herein can perform eye examinations semi- of completely autonomously. That is, an ophthalmologist or optometrist may provide little or no guidance during the examination. However, network-accessible HMDs may allow ophthalmologists and/or optometrists to remotely supervise and participate in examinations.

At block 704, the HMD conducts a test. The test may, for example, measure visual acuity or visual field. At block 706, the HMD acquires a result that is audible, gestural, textual, etc., in nature. For example, the patient may audibly recite a set of letters or numbers that are presented to one or both eyes. Once the result is acquired, the HMD (or another distinct computing system) can determine whether the result is abnormal in any way. Abnormal results can include wrong answers, incomplete or incomprehensible answers, etc. Abnormal results may also be detected by comparing the preliminary result to results from previous examinations.

If no abnormalities are detected, the examination can continue, as shown at block 708. That is, the examination can end or another test can be conducted. However, if an abnormality is detected, the HMD or distinct computing system can determine whether any potential causes exist for the abnormal result, as shown at block 710. Potential causes can include misreadings and equipment malfunctions (e.g., erroneous voice recognition), as well as potential eye diseases. Typically, the HMD or distinct computing system generates a likelihood for each potential cause. The likelihood represents the estimated probability the potential cause is the actual cause of the abnormal result.

At block 712, the one or more tests that make up the eye examination can be modified based on the abnormal result, potential causes, likelihoods, or some combination thereof. More specifically, the content of the examination can be adapted based on the results from one or more tests. For example, the HMD may add, modify, or remove tests in response to identifying a zone of visual weakness, discovering what the patient does for a living, etc. These personalized eye examinations, which can be updated in real-time based on recently-acquired results, are more likely to provide valuable insights than other eye examination systems.

Figure 8:
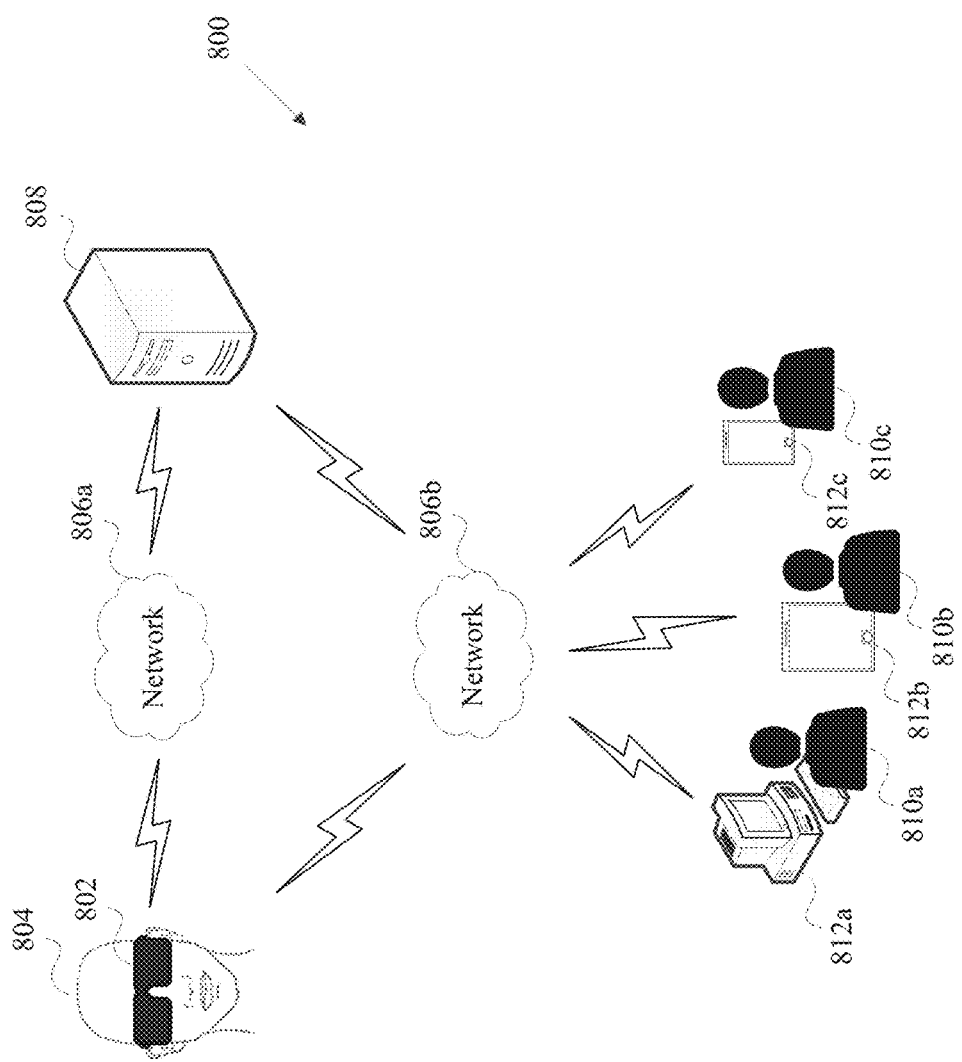
FIG. 8 is a generalized block diagram depicting components of a system for performing eye examinations as may be employed in some embodiments.

FIG. 8 is a generalized block diagram depicting components of a system 800 for performing eye examinations as may be employed in some embodiments. In some embodiments, the HMD 802 is communicatively coupled to a distinct computing system 808 (e.g., server) over a network 806a, such as the Internet. The HMD 802 and/or distinct computing system 808 can perform some or all of the methods described herein. That is, the system 800 can be distributed amongst the HMD 802 and the distinct computing system 808.

In some embodiments, one or more network-accessible devices 812a-c that are controlled by ophthalmologists, optometrists, etc., 810a-c are communicatively coupled to the HMD 802, the distinct computing system 808, or both. One or more networks 806a-b can be used to communicatively couple the various components of the system 800. Network 806a can be the same as, or distinct from, network 806b.

Such a configuration allows ophthalmologists, optometrists, etc., 810a-c to supervise the patient 804 while the eye examination is conducted. While the HMD 802, distinct computing system 808, and network-accessible devices 812a-c are depicted as wirelessly communicating with one another, wired connections are also possible and, in some embodiments, may be preferred.

Computer System

Figure 9:
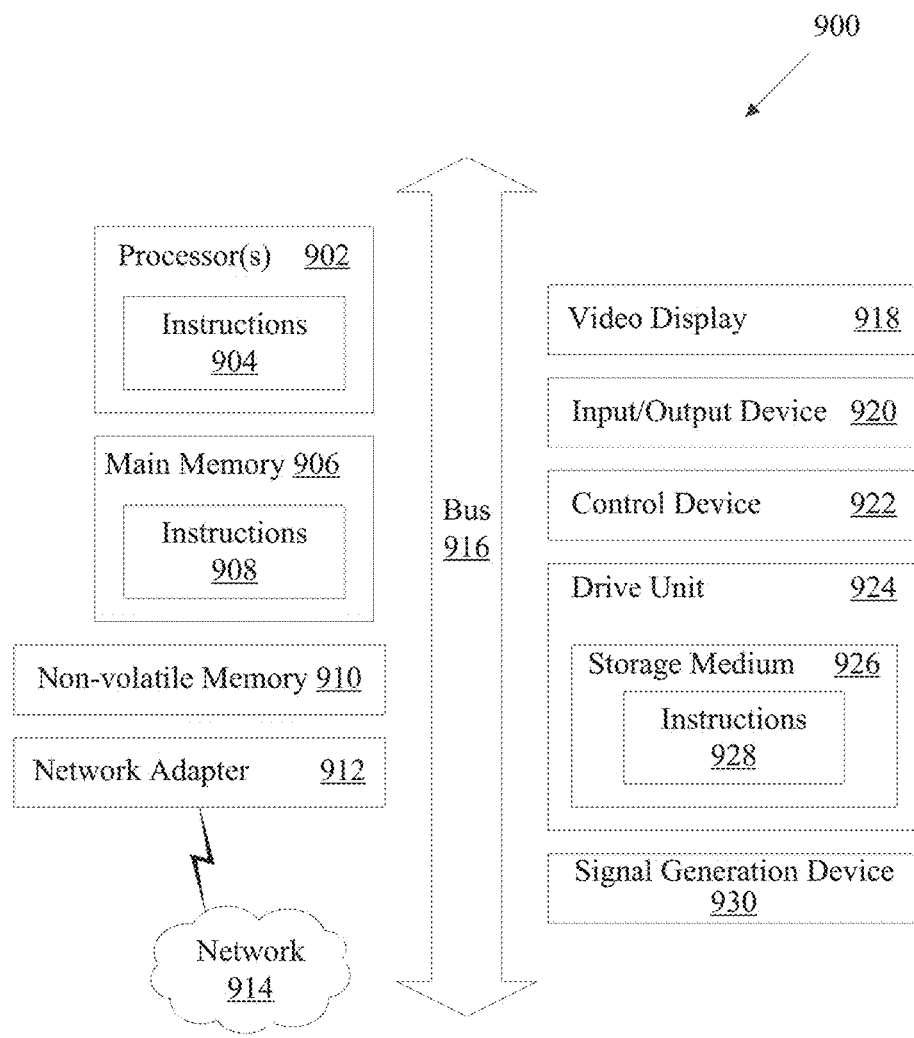
FIG. 9 is a block diagram illustrating an example of a computer system in which at least some operations described herein can be implemented according to various embodiments.

FIG. 9 is a block diagram illustrating an example of a computing system 900 in which at least some operations described herein can be implemented. The computing system may include one or more central processing units ("processors") 902, main memory 906, non-volatile memory 910, network adapter 912 (e.g., network interfaces), video display 918, input/output devices 920, control device 922 (e.g., keyboard and pointing devices), drive unit 924 including a storage medium 926, and signal generation device 930 that are communicatively connected to a bus 916. The bus 916 is illustrated as an abstraction that represents any one or more separate physical buses, point to point connections, or both connected by appropriate bridges, adapters, or controllers. The bus 916, therefore, can include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

In various embodiments, the computing system 900 operates as a standalone device, although the computing system 900 may be connected (e.g., wired or wirelessly) to other machines. In a networked deployment, the computing system 900 may operate in the capacity of a server or a client machine in a client-server network environment, or as a peer machine in a peer-to-peer (or distributed) network environment.

The computing system 900 may be a server computer, a client computer, a personal computer (PC), a user device, a tablet PC, a laptop computer, a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, or any machine capable of executing a set of instructions (sequential or otherwise) that specify actions to be taken by the computing system.

While the main memory 906, non-volatile memory 910, and storage medium 926 (also called a "machine-readable medium) are shown to be a single medium, the term "machine-readable medium" and "storage medium" should be taken to include a single medium or multiple media (e.g., a centralized or distributed database, and/or associated caches and servers) that store one or more sets of instructions 928. The term "machine-readable medium" and "storage medium" shall also be taken to include any medium that is capable of storing, encoding, or carrying a set of instructions for execution by the computing system and that cause the computing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 904, 908, 928) set at various times in various memory and storage devices in a computer, and that, when read and executed by one or more processing units or processors 902, cause the computing system 900 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices 910, floppy and other removable disks, hard disk drives, optical disks (e.g., Compact Disk Read-Only Memory (CD ROMS), Digital Versatile Disks, (DVDs)), and transmission type media such as digital and analog communication links.

The network adapter 912 enables the computing system 900 to mediate data in a network 914 with an entity that is external to the computing device 900, through any known and/or convenient communications protocol supported by the computing system 900 and the external entity. The network adapter 912 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 912 can include a firewall which can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

Other network security functions can be performed or included in the functions of the firewall, can include, but are not limited to, intrusion-prevention, intrusion detection, next-generation firewall, personal firewall, etc.

As indicated above, the techniques introduced here implemented by, for example, programmable circuitry (e.g., one or more microprocessors), programmed with software and/or firmware, entirely in special-purpose hardwired (i.e., non-programmable) circuitry, or in a combination or such forms. Special-purpose circuitry can be in the form of, for example, one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

What is claimed is:

1. A head-mounted display (HMD) for conducting eye examinations, the HMD comprising:
   a frame that rests upon a head of a patient during use;
   a left optical display surface configured to present digital images to a left eye;
   a right optical display surface configured to present digital images to a right eye;
   an image display system that is able to
      visibly present digital images only to the left eye on the left optical display surface while visibly presenting nothing to the right eye on the right optical display surface,
      visibly present digital images only to the right eye on the right optical display surface while visibly presenting nothing to the left eye on the left optical display surfaces, and
      visibly present digital images to the left eye and the right eye simultaneously on the left and right optical display surfaces,
      wherein the frame is designed such that
         nothing can be seen by the right eye when digital images are presented only to the left eye, and
         nothing can be seen by the left eye when digital images are presented only to the right eye,
      so as to enable examining the left and right eyes individually;
   an audio sensor configured to be able to autonomously record an audible response given by the patient during an eye examination;
   a speaker configured to be able to autonomously pose an audible question that can be heard by the patient;
   a speech recognition module configured to be able to autonomously identify one or more relevant keywords within the audible response; and
   an analysis module configured to be able to autonomously
      compare the one or more relevant keywords to a master set of keywords known to represent a correct response to the audible question,
      determine that at least one relevant keyword does not match the master set of keywords, and
      adapt the eye examination in real time in response to the keywords.

2. The HMD of claim 1, further comprising:
   one or more sensors configured to track ambient conditions substantially likely to influence test results acquired during the eye examination.

3. The HMD of claim 2, wherein the ambient conditions include glare, brightness, humidity, or some combination thereof.

4. The HMD of claim 1, wherein the patient can select a visual environment that is presented on the left optical display surface, the right optical display surface, or both during some or all of the eye examination.

5. The HMD of claim 4, wherein the visual environment is an artificial virtual environment selected by the patient.

6. The HMD of claim 1, wherein speaker is configured to pose statements and questions designed to elicit audible responses from the patient.

7. The HMD of claim 6, wherein the audible responses specify what is being shown on the left optical display surface or the right optical display surface, a vision problem experienced by the patient, or both.

8. The HMD of claim 6, wherein the audio sensor records utterances given by the patient throughout the eye examination.

9. The HMD of claim 1,
   wherein the one or more relevant keywords include
      a term indicative of a potential eye condition, or
      a term indicative of an incorrect response to the audible question.

10. The HMD of claim 9, wherein the analysis module is further configured to:
    generate a notification indicative of whether the patient passed a given test of the eye examination;
    store the notification within a memory; and
    transmit the notification to a remote computing device.

11. The HMD of claim 1, wherein the eye examination is adapted in real time while one or more tests are being performed.

12. The HMD of claim 1, wherein adapting the eye examination includes performing at least one of:
    modifying an existing test scheduled to be performed during the eye examination;
    removing an existing test scheduled to be performed during the eye examination; and
    adding a new test to be performed during the eye examination.

13. A head-mounted display comprising:
    a frame that rests upon a head of a patient during use;
    an optical display surface configured to present digital images;
    an image display system configured to generate digital images for display to the patient;
    a speaker configured to autonomously pose an audible question that can be heard by the patient;
    an audio sensor configured to autonomously record an audible response given by the patient during an eye examination;
    a processor; and
    a memory including instructions that, when executed by the processor, cause the processor to autonomously:
       identify one or more relevant keywords within the audible response;
       determine whether the audible response is indicative of a correct response to the audible question by comparing the one or more relevant keywords to a master set of keywords known to represent the correct response;
       determine that at least one relevant keyword does not match the master set of keywords; and
       adapt the eye examination in real time in response to the keywords.

14. The head-mounted display of claim 13, wherein the audible question posed by the speaker includes a recording, a live utterance, or both.

15. The head-mounted display of claim 13, wherein the image display system is able to visibly present digital images only to a left eye while visibly presenting nothing to a right eye, only to the right eye while visibly presenting nothing to the left eye, and to both the left eye and the right eye simultaneously, so as to enable examining the left and right eyes individually.

16. The head-mounted display of claim 13, wherein the optical display surface is one of multiple optical display surfaces connected to the frame.

17. The head-mounted display of claim 13,
    wherein execution of the instructions further causes the processor to:

store the audible response, the at least one relevant keyword, and a summary indicating whether the patient passed the eye examination within a database, wherein the database is remotely accessible by an ophthalmologist or an optometrist.

18. The head-mounted display of claim 13, wherein the at least one relevant keyword is indicative of a possible presence of an eye condition, and wherein adapting the eye examination in real time comprises:

adding a new test to the eye examination that is designed to reveal whether a symptom of the eye condition is present.

* * * * *